(12) United States Patent
Dunham

(10) Patent No.: US 7,891,106 B2
(45) Date of Patent: Feb. 22, 2011

(54) GROWTH CHART DEVICE

(76) Inventor: Timothy Louis Dunham, Box 305, 112b Collins Street, Creighton, SK (CA) S0P 0A0

( * ) Notice: Subject to any disclaimer, the term of this patent is extended or adjusted under 35 U.S.C. 154(b) by 0 days.

(21) Appl. No.: 12/688,974

(22) Filed: Jan. 18, 2010

(65) Prior Publication Data

US 2010/0223799 A1 Sep. 9, 2010

Related U.S. Application Data

(60) Provisional application No. 61/157,955, filed on Mar. 6, 2009.

(51) Int. Cl.
*A61B 5/103* (2006.01)
*G01B 3/04* (2006.01)
(52) U.S. Cl. .......................... 33/512; 33/486
(58) Field of Classification Search ............... 33/483, 33/484, 485, 486, 512
See application file for complete search history.

(56) References Cited

U.S. PATENT DOCUMENTS

| | | | | |
|---|---|---|---|---|
| 1,974,085 A | * | 9/1934 | Shields et al. .................. | 33/512 |
| 2,215,884 A | * | 9/1940 | Runge .......................... | 33/512 |
| 4,118,868 A | * | 10/1978 | Johnson ....................... | 33/512 |
| 6,226,881 B1 | * | 5/2001 | Landauer ..................... | 33/512 |
| 6,519,868 B1 | * | 2/2003 | Pryor et al. ................... | 33/485 |
| 7,103,983 B2 | * | 9/2006 | Lehavi ....................... | 33/512 |
| 2004/0111909 A1 | * | 6/2004 | Pourmanafzadeh .......... | 33/512 |
| 2010/0088915 A1 | * | 4/2010 | Neff ............................. | 33/759 |

* cited by examiner

*Primary Examiner*—G. Bradley Bennett
(74) *Attorney, Agent, or Firm*—Ade & Company Inc.; Kyle R. Satterthwaite; Ryan W. Dupuis

(57) ABSTRACT

A growth chart device features presenting a wall facing side and an opposing chart side with a measuring scale extending along the chart side along a lengthwise dimension of the chart body. A marking area is defined on the chart side of the chart body proximate the measuring scale to receive markings at different positions along the measuring scale at different times to track a height of an individual. At least one door is pivotally mounted on the chart body and movable between open and closed positions in which at least a portion of the chart side of the chart body is respectively uncovered and covered to give selective control over access to said portion.

20 Claims, 7 Drawing Sheets

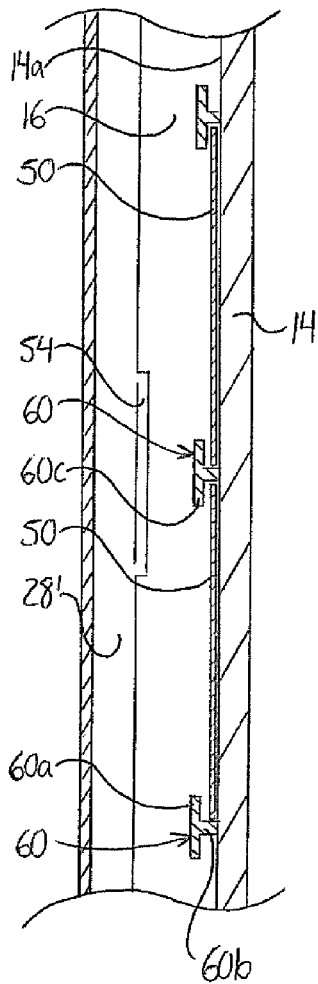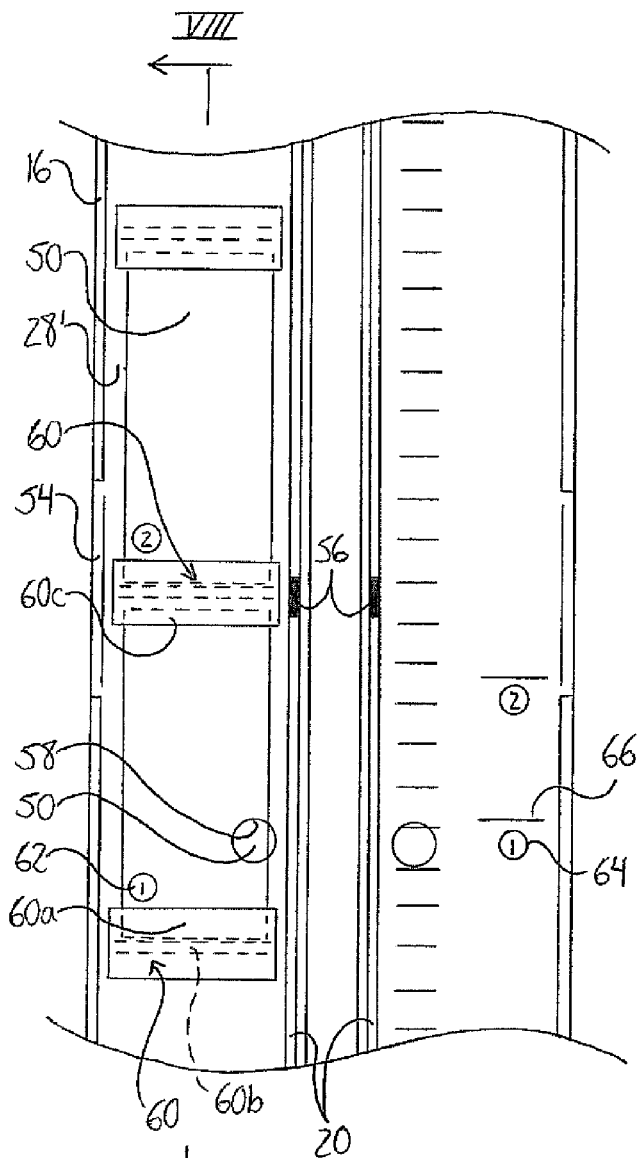
FIG. 8
FIG. 7

GROWTH CHART DEVICE

This application claims benefit under 35 U.S.C. 119(e) of U.S. Provisional Patent Application Ser. No. 61/157,955, filed Mar. 6, 2009.

FIELD OF THE INVENTION

This invention relates generally to growth charts, and more particularly to a growth chart device having at least one door for selective covering and uncovering of items or information displayed along a scale of the growth chart.

BACKGROUND OF THE INVENTION

It is well known to mount a growth or height chart to a wall in a vertical orientation so that the growth of a child can be measured and tracked by having the child stand against the wall and mark the child's height along a measuring scale pre-printed on the chart. It is known to provide a marking or writing surface adjacent the measuring scale in order to facilitate the recording of personalized notes at different stages in the child's life and to mount pictures or photographs to the chart to similarly reflect events that occurred at times when the child had grown to reach certain heights.

Such mounting of pictures on growth charts is taught in U.S. Pat. Nos. 6,519,868; 1,974,085 and 4,118,868, the latter two of which also teach charts that are foldable into a compact storage or book-like form, in which the pictures and markings adjacent the measuring scale are hidden from sight.

However, there remains room for further improvement in growth chart devices that allow selective enclosing or containment of their contents.

SUMMARY OF THE INVENTION

According to a first aspect of the invention there is provided a growth chart device comprising:

a chart body presenting a wall side intended to face a wall or other vertical structure to which the growth chart is to be mounted and a chart side opposite said wall side;

a measuring scale defined on the chart side of the chart body to extend along a lengthwise dimension of the chart body to be vertically oriented when mounted to the wall or other vertical structure;

a marking area defined on the chart side of the chart body proximate the measuring scale to receive markings at different positions along the measuring scale at different times to track a height of an individual; and at least one door pivotally mounted on the chart body and movable between open and closed positions in which at least a portion of the chart side of the chart body is respectively uncovered and covered to give selective control over access to said portion.

Preferably said portion of the chart side of the chart body selectively enclosable by the at least one door includes at least part of the measuring scale.

Preferably there is provided a sliding indicator slidably mounted to the chart body for movement along the lengthwise dimension thereof to a position indicating the height of the individual along the measuring scale.

Preferably the at least one door comprises a pair of doors mounted on the chart body to close over respective portions of the chart side of the chart body on opposite sides of the sliding indicator.

Preferably there is provided a rail structure along which the sliding indicator is slidable and which projects from the chart side of the chart body past the sliding indicator to form a stop against which each door abuts in the closed position.

Preferably the rail structure comprises a pair of opposing rails each having a track formed therein into which features of the sliding indicator project from between the opposing rails.

Preferably at least one of the tracks comprises a through-slot in a respective one rail of the opposing rails.

Preferably a projecting portion of the sliding indicator projects along the chart side of the chart body toward the measuring scale.

Preferably a measuring arm of the sliding indicator is pivotable between storage and measuring positions extending along and projecting away from the chart side of the chart body respectively.

Preferably the measuring scale and the marking area are defined on a same side of the sliding indicator.

Preferably the sliding indicator is centrally located along a widthwise dimension of the chart body.

Preferably there is provided a display area defined on the chart side of the chart body on a side of a central lengthwise axis thereof opposite the marking area, wherein the at least one door comprise a pair of doors each arranged to selectively close over at least part of a respective one of the display and marking areas.

Preferably each door is pivotable about an axis parallel to the lengthwise dimension of the chart body.

Preferably each door is hinged to the chart body along a lengthwise edge of the chart body.

The at least one door may comprise a display door carrying a plurality of picture holders thereon, in which case the picture holders are preferably defined on an exterior side of the display door facing away from the selectively coverable portion of the chart side of the chart body.

Preferably the chart body has fastener holes passing therein for passage of fasteners therethrough from the chart side of the chart body to secure the device to the wall or other vertical structure.

The growth chart device may be provided in combination with a plurality of picture supports selectively attachable to the chart body on the chart side thereof at different positions along the lengthwise dimension of the chart body to support pictures thereon.

Each picture support preferably has a cross-section presenting a projecting portion arranged to project outward from the chart side of the chart body when attached thereto and at least one retaining portion projecting to a respective side of the projecting portion to extend upward or downward along the chart side of the chart body when attached thereto.

Preferably each photograph support comprises two retaining portions projecting to opposing sides of the projecting portion to extend upward and downward along the chart side of the chart body when attached thereto.

The growth chart device may be used in combination with multiple pairs of labels, each pair comprising two labels having matching indicia for application of one of the two labels to a picture and the other of the two labels to a marked position along the measuring scale corresponding to a height of a person shown in the picture at a period of time when the picture was taken.

The matching indicia of at least some of the pairs of labels may comprise matching numbers.

BRIEF DESCRIPTION OF THE DRAWINGS

In the accompanying drawings, which illustrate exemplary embodiments of the present invention:

FIG. 7 is a partial front elevational view of a second embodiment growth chart device featuring transparent doors and stick-on photograph supports and labels.

FIG. 8 is a partial cross-sectional view of the second embodiment growth chart as taken along line VIII-VIII of FIG. 7.

DETAILED DESCRIPTION

Figure 4:
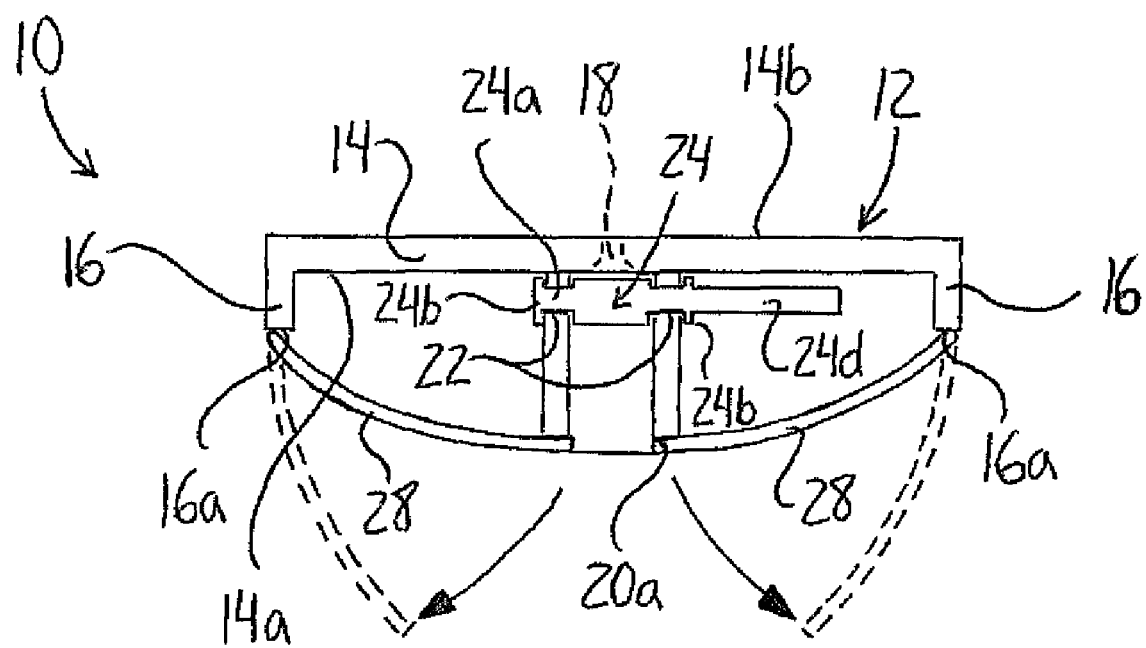
FIG. 4 is an overhead plan view of the first embodiment growth chart device with a top panel thereof removed for illustration.

With reference to FIG. 4, a growth chart device 10 according to the first embodiment features an elongated main body 12 having a squared off shallow U-shape in a cross sectional plane cutting through the body normal to a central axis defining its lengthwise dimension. The body features a rectangular rear wall or panel 14 from which two parallel side walls 16 perpendicularly project at the two lengthwise sides of the rear wall 14 over the full length thereof. A plurality of fastener holes 18 pass through the rear wall 14 at spaced positions along a central lengthwise axis thereof centered between the side walls 16 to enable securing of the main body 12 to a vertical planar surface provided by a wall or other vertically projecting structure by use of fasteners passed through the holes 18. As shown, the fastener holes 18 may be countersunk screw holes so that respective screws fed through the holes from a front side 14a of the rear wall 14 do not project forwardly from the front side 14a once fully threaded into the structure against which the opposite rear side 14b of the rear wall 14 is placed flushed against. As shown, the rear wall may be thicker than the side walls for improved strength to prevent breakage when mounting to a wall.

On opposite sides of the central lengthwise axis of the rear wall 14, a pair of rails 20 are fixed to the front face 14a of the rear wall and extend parallel to the lengthwise axis between them. Each rail 20 extends the full length of the rear wall 14 and has the general structure of a elongate rectangular panel having its shorter width dimension projecting perpendicularly from the front face 14a of the rear wall 14 with a central longitudinal through-slot 22 formed in the otherwise solid rail over nearly the full length thereof. The slot 22 is open to the top edge of the rail 20 at its top end and extends toward, without reaching, the bottom end of the rail proximate the bottom end of the rear wall 14, thereby situating the bottom end of the slot a short distance above the bottom of the rear wall 14.

Figure 5A:
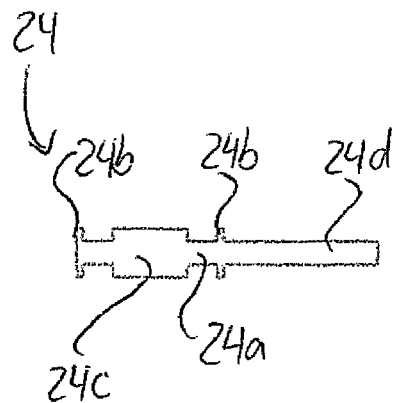
FIGS. 5A, 5B and 5C are overhead plan, front elevational and side elevational views respectively of the sliding indicator of the first embodiment growth chart device as would be seen its stowed position.
Figure 5B:
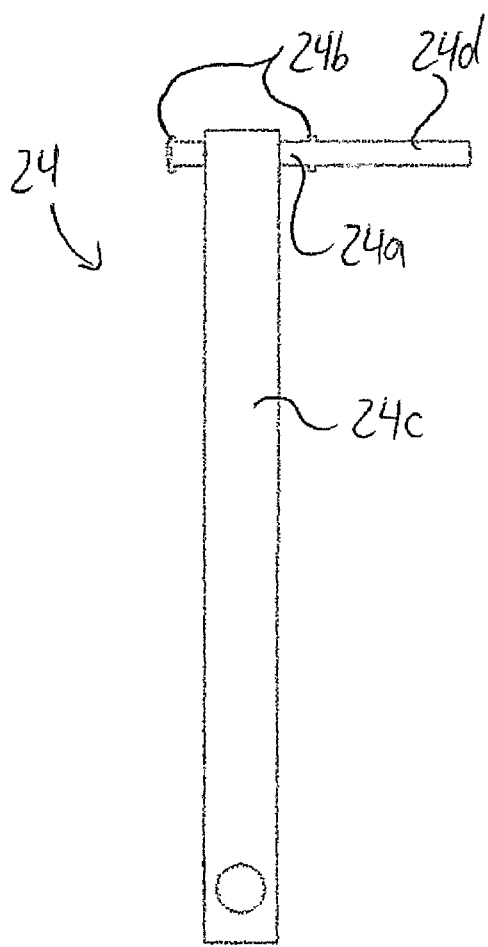
Figure 5C:
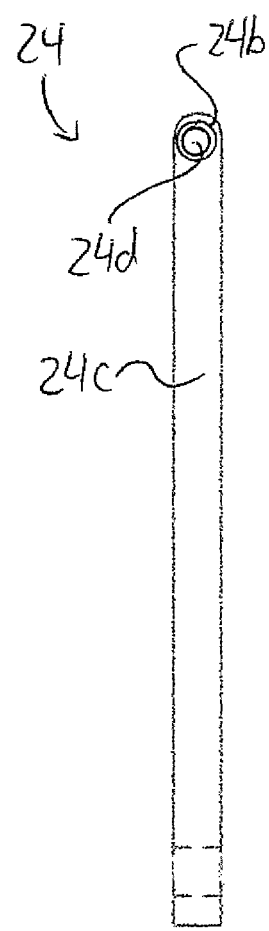

Features of a sliding indicator 24, which is shown in isolation in FIG. 5, are received within the slots 22 of the two parallel rails 20 to enable guided sliding of the indicator therealong in upward and downward directions along the central lengthwise axis of the rear wall 14. The sliding indicator 24 features a cylindrical rod or shaft-like portion 24a having a diameter less than a width of each slot 22 so that the rod portion 24a passes through both slots 22 from between the two rails 20. A pair of annular flanges 24b project radially outward from the rod portion 24a at spaced apart positions therealong just outside the rails 20 through which the rod portion 24a passes. The outer diameter of each flange 24b is greater than the slot width in the rail 20 there adjacent so that lateral motion of the sliding indicator 24 in directions transverse to the lengthwise axis along which the indicator is slidable in the slots 22 and tilting of the rod portion 24a out of a horizontal orientation perpendicular to the lengthwise axis is limited by contact between the flanges and the rails. By blocking motion of the ends of the rod portion into the space between the rails, the flanges prevent the slider from falling therein. The rails and travel slots formed therein define tracks or a path along which the indicator can be linearly slid or displaced.

Figure 3:
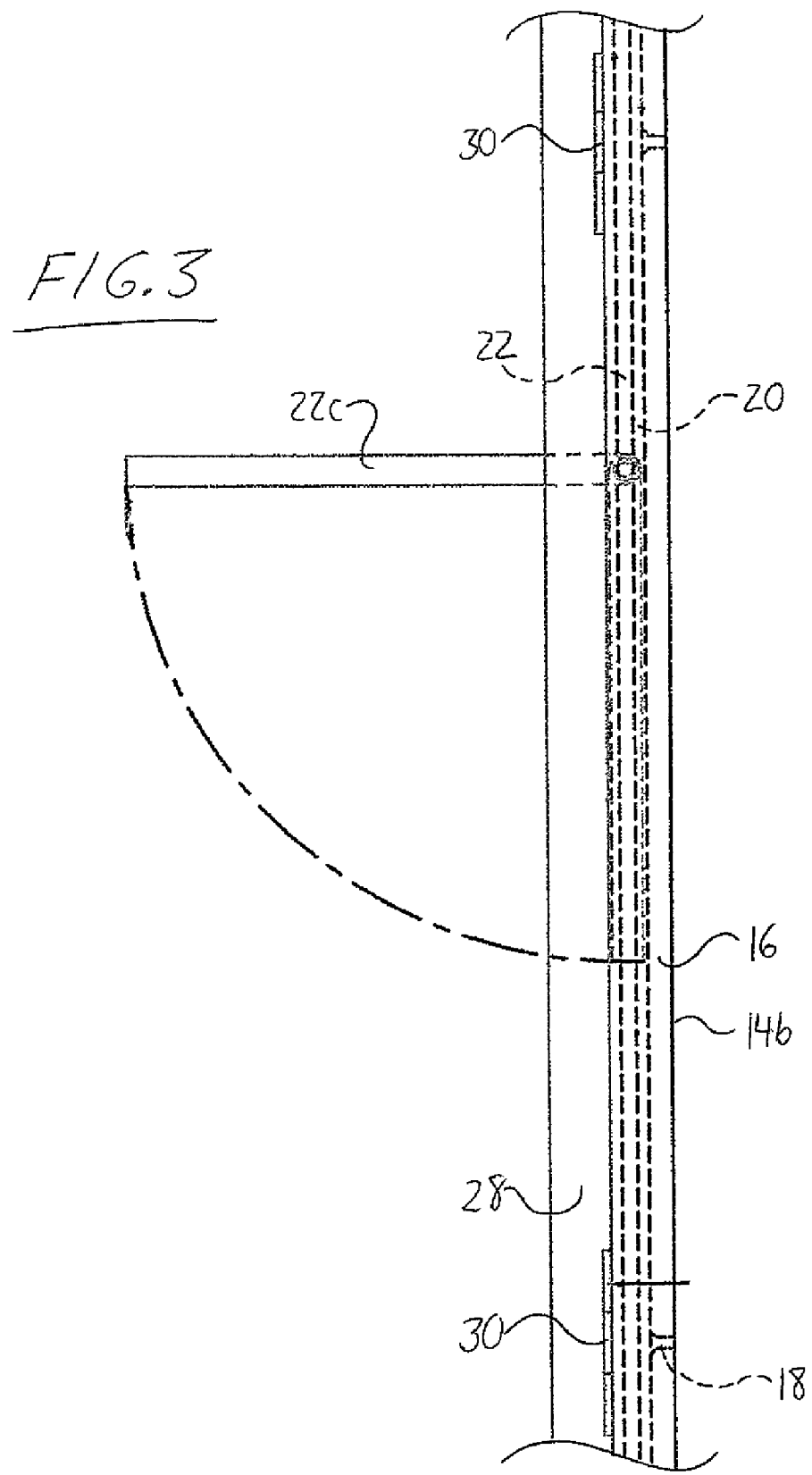
FIG. 3 is a close up side elevational view of the first embodiment growth chart device with the sliding indicator arm in a deployed measuring position.

A measuring arm portion 24c of the sliding indicator 24 projects from the rod portion 24a to one side thereof parallel to a single radial direction of the cylindrical rod portion 24a. The width of each of the two equally dimensioned slots 22 in the rails 20 slightly exceeds the diameter of the rod portion 24a of the sliding indicator 24 so that the rod portion 24a is pivotal about the horizontal axis around which the rod portion's cylindrical periphery closes. In a normal or natural orientation of the sliding indicator 24, the weight of the measuring arm 24c causes it to hang downward from the rod portion 24a along the rear wall 14 in a stowed or storage position between the two rails 20. However, the measuring arm 24 can be manually gripped by its distal end opposite the rod portion 24a to pull it away from the rear wall 14 and thus pivot the entire sliding indicator 24 about the axis of the rod portion 24a into a deployed orientation shown in FIG. 3 where the arm projects perpendicularly outward away from the rear wall 14. In this deployed condition, the sliding indicator can be manually slid up the rails 20 to a height along the rear wall 14 sufficient to accommodate the child to be measured beneath the arm, and then subsequently lowered into a position where the projecting measuring arm 24c rests atop the child's head.

Referring again to FIG. 5, a width of the measuring arm 24c measured along the axis of the rod portion 24a is less than the distance between the flanges 24b along the rod axis so as to leave space between each flange and the nearest side of the measuring arm 24c. These exposed areas of the rod portion 24a left unobstructed by the measuring arm between the flanges are the parts of the rod portion that pass through the respective slots in the rails 20. A cylindrical projecting portion 24d of the sliding indicator 24 is coaxial with the rod portion 24a and extends to a side of one of the two flanges 24b opposite the rod portion outside the rails 20. A measuring scale 26 is featured on the front face 14a of the rear wall 14 on the same side of one of the rails to which the projecting portion 24d of the sliding indicator projects along the rear wall. This way, when the measuring arm 24c of the sliding indicator 24 is positioned atop the child's head as described above, the projecting portion 24d of the indicator positioned over the measuring scale indicates the child's height on the scale 26, thereby defining a pin for use as a marking reference along the scale mounted behind the slider. The height scale 26 may include either one or both of metric and imperial or English units. In a known manner, the numbering of the scale begins at a height at which the bottom of the scale is intended to be supported when the device is mounted to a vertical surface of a wall or other structure. For example, a chart on which the scale begins at two feet and zero inches would include instructions on mounting the chart body at an appropriate height to position the start of the scale twenty-four inches above the floor.

The illustrated sliding indicator is a one-piece design produced as a molded plastic piece where the rod and projecting portions 24a, 24d are of equally dimensioned circular cross section. The measuring arm 24c has the form of a rectangular parallelepiped that has been rounded at one end to curve arcuately through 180 degrees concentrically about the axis of the rod portion with the thickness of the arm, corresponding to the diameter of its semicircular end, slightly exceeding the diameter of the equally sized flanges 24b. A through hole 24e passes through the measuring arm 24c in a direction normal to the opposing surfaces connected by its curved or rounded end at a position proximate a distal end of the measuring arm opposite the rod portion 24a. This defines a finger hole by which a user can grasp the hanging arm when stowed between the rails 20 by placing a fingertip within the hole to frictionally grip the arm and lift it the distal end of the arm through an arcuate path into the deployed measuring position.

A strip of the front side or face 14a of the rear wall on a side of the scale 26 opposite the rails 20 defines a marking area either left blank or equipped with a suitable writing surface for marking of the child's height along the scale at the time a measurement is taken. The markings may be made using a writing utensil or by cutting, notching, punching or otherwise making visible markings, written notes, drawings or illustrations. On a side of the rails 20 opposite the scale 26, the entire corresponding side of the rear wall's front face 14a may be left open to accommodate further markings or posting of additional materials such as pictures, photos, illustrations, ribbons or other personal items reflective of a time in the child's life corresponding to a marked height along the scale 26.

To facilitate selective concealment and display of the markings and photographs or other materials or information presented on the front side 14a of the rear wall 14, the growth chart device 10 features a pair of doors 28 mounted to the chart body 12 on opposite ones of the side walls 16 by hinges 30. In the illustrated embodiment, each door is pivotally secured to the respective side wall 16 at a distal end 16a thereof opposite the rear wall 14 by three hinges 30 spaced apart along the vertical lengthwise dimension of the narrow side wall 16 so that the door is pivotal about a vertical axis. In a closed position, each door 28 extends from the respective side wall 16 to the one of the two rails 20 nearest thereto. As shown in FIG. 4, each door may be curved or arcuate in a cross sectional horizontal plane perpendicular to the rear wall's lengthwise axis to present, when closed, a convex exterior side facing away from the rear wall 14 and a concave interior side facing toward the rear wall 14 when closed. In the illustrated embodiment, the rails 20 project further from the rear wall 14 than the side walls 16 and the doors are of a sufficient width to close over distal edges 20a of the rails 20 opposite the rear wall 14 so that these distal edges act as stops against which the inner side of the door 28 abuts at a distal end portion of the door's width opposite the hinged connection to the side wall 16. Movement of the door is illustrated in FIG. 4 by showing the doors 28 in broken lines as they swing outward into open positions exposing the portions of the rear wall front face 14a on opposite sides of the rails 20. In the illustrated embodiment, the doors do not close over one another or over the space between the rails 20, although such more fully closing embodiments are certainly possible.

Figure 1:
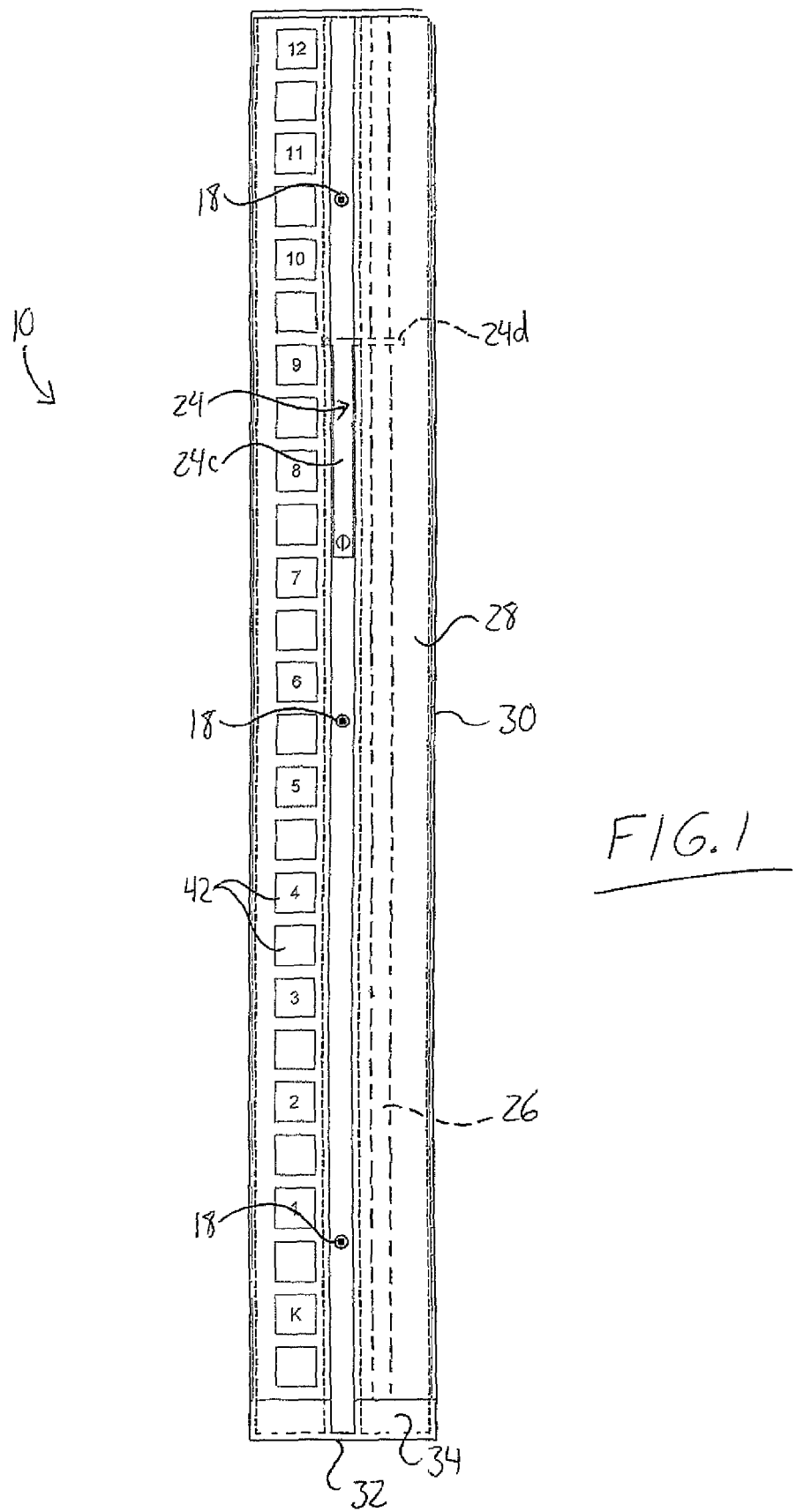
FIG. 1 is a front elevational view of a growth chart device according to a first embodiment of the present invention.
Figure 2:
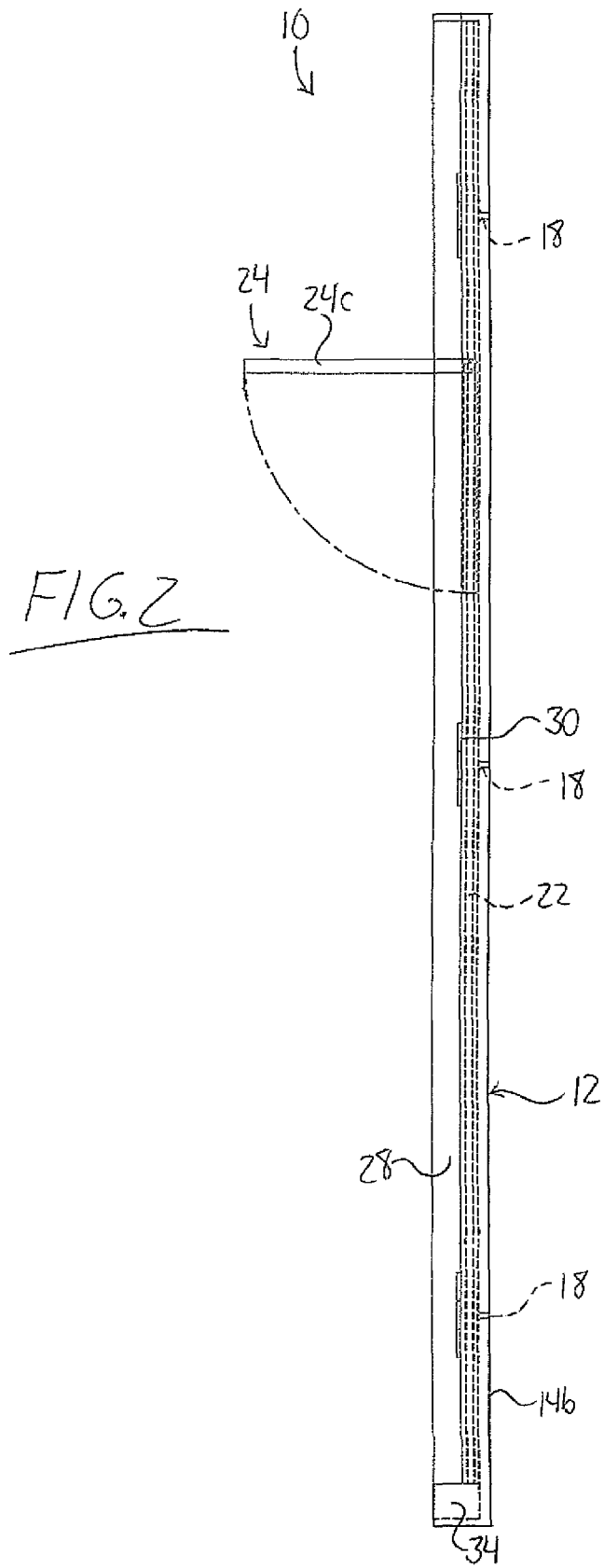
FIG. 2 is a side elevational view of the first embodiment growth chart device with a sliding indicator arm thereof in a stowed position.

With reference to FIG. 1, the doors extend the full length of the slots 22 in the rails 20. Beneath the slots 20, an intact rectangular portion of each rail extends a short distance downward from the slot 22 and connects to a horizontal bottom panel 32 of the chart body 12, defining a lowermost extent or base of the growth chart device or gauge 10. The bottom panel or plate 32 has rear and side edges that are flush with the rear or wall side 14b of the rear wall 14 and the outer sides of the side walls 16, and a curved front edge flush with the exterior faces of the doors 28 when closed. The bottom panel fully spans the area bound by these edges, thereby closing off the bottom end of the channel or space defined between the rails 20 and the bottom end of the space defined between each door 28 and the rear wall 14 between the respective side wall 16 and rail 20. A pair of curved front walls 34 flush with the curved front edge of the bottom panel 32 project upward from the bottom panel to the bottom edges of the doors, each spanning from the distal end of a respective side wall 16 of the chart body 12 to the distal end of the nearest rail 20 to give the growth chart device a fully closed look on both sides of the rail structure with the doors in the closed positions.

Figure 6A:
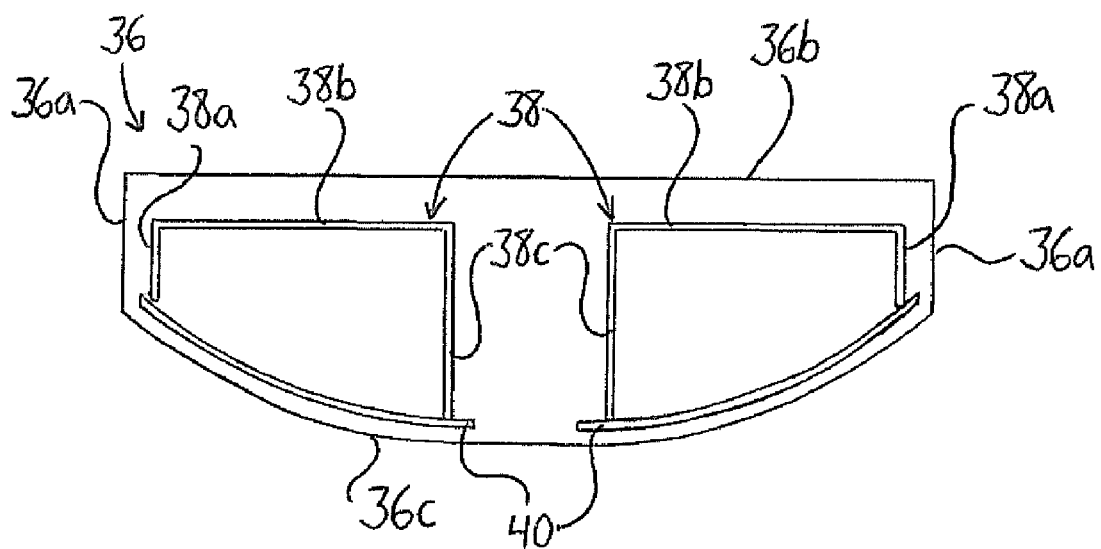
FIGS. 6A and 6B are bottom plan and rear elevational views respectively of a top panel of the first embodiment growth chart device.
Figure 6B:
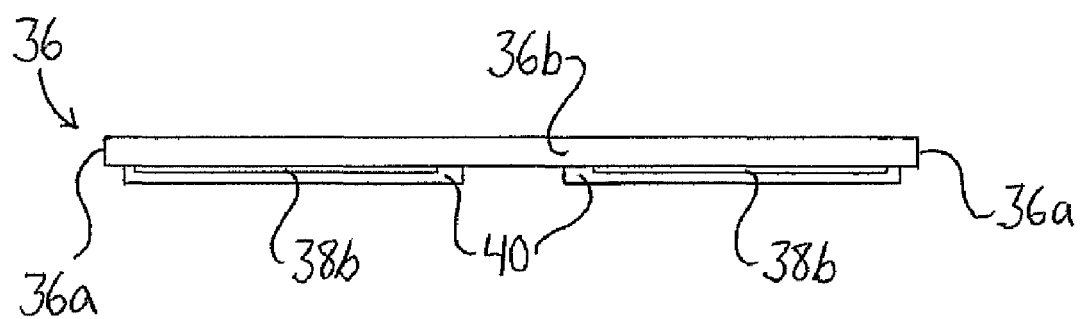

FIG. 6 shows a top panel 36 of the chart body 12 to be positioned atop the rear and side walls 14, 16 to close off a top end of the chart device in a manner similar to the bottom panel 32. Like the bottom panel or plate 32, the top panel or plate 36 has two linear side edges 36a and a linear rear edge 36b to sit flush with the planar outer sides of the side walls 16 and the planar rear side 14b of the rear wall 14, and a curved front edge 36c to sit flush with the exterior faces of the closed doors 28. The top panel 36 fully spans the area bound by these edges, thereby closing off the top end of the channel or space defined between the rails 20 and the top end of the space defined between each door 28 and the rear wall the rear wall 14 between the respective side wall 16 and rail 20. The top panel 36 thus has the same shape in plan as the bottom panel 32, but differs in that it includes assembly index ridges 38 and door stop ridges 40.

The assembly ridges include side wall ridges 38a, rear wall ridges 38b and rail structure ridges 38c projecting a short perpendicular distance from a bottom face 36d of the top panel 36. Each side wall ridge 38a extends parallel to a respective one of the two side edges 36a of the top panel 36 at a distance inward therefrom corresponding to the thickness of the respective chart body side wall 16. Each of the two rear wall ridges 38b extends perpendicularly from a respective one of the side wall ridges 38a at an end thereof nearest the rear edge 36b of the top panel 36 so as to extend parallel to the rear edge 36b at a distance therefrom corresponding to the thickness of the rear wall 14 of the chart body 12. Each of the two rail structure ridges 38c extends perpendicularly from a respective rear wall ridge 38b at an end thereof opposite the respective side wall ridge away from the rear edge 36b of the top panel. The distance left between the rail structure ridges 38c at the center of the top panel 36 equals the distance between the outer sides of the two rails 20 of the chart body 12. By placing the downwardly depending rear wall, side wall and rail ridges against the front face of the rear wall, inner faces of the side walls and outer faces of the rails respectively during lowering of the top panel onto the chart body, the assembly ridges positively locate the top panel atop the chart body for a flush fit instead of relying on visual alignment during assembly.

Each of the two door stop ridges 40 arcuately curves from proximate an end of a respective one of the side wall ridges 38a in a concentric manner with a respective portion of the curved front edge 36c of the top panel 36 at a distance inward therefrom corresponding to a thickness of the respective door 28. As shown, the door stop ridges 40 may extend past the respective rail structure ridges 38c, and the distal end of each door may thus contact its respective door stop ridge rather than the distal edge of the respective rail 20 at the top end of the door, but flexibility in the door or play in its hinge mounting may mean that the distal edge of the rail still provides a positive stop for the door at positions lower down therealong.

As shown in FIG. 1, one door 28 may have picture frames 42 mounted thereon or defined thereby to facilitate display of photographs or pictures on the door's exterior. It will be appreciated that both doors may be provided with such features and that the frames or supports may alternatively be provided on an interior side of the door for selective display when the doors are opened to face their interior sides outward.

It may be possible to produce the described chart bodies, doors and sliding indicators as molded plastic parts that can be produced efficiently and reliably on relatively large scales. The rear wall, side walls and slotted rail walls of the chart body may be integral parts of a single molded piece into which a separately molded plastic slider may be inserted from the open top ends of the rail slots for completion of the assembly by installation of the top and bottom panels. The bottom panel and front walls may be a single integral body of molded plastic. Alternatively, the chart device may lack the illustrated and described front walls, in which case the doors may extend fully down to the bottom panel past the closed lower end of the rail slots. The top panel and its ridges also may be produced as a single integral plastic piece. Where the chart bodies are produced in this manner, the hinges may be molded into place in the side walls during to eliminate hinge installation as a later assembly step in the production process.

It will be appreciated that other embodiments may make use of different numbers, sizes, orientations or positions of doors in order to provide the same ability to selectively display and conceal markings and other recordings or information on one or more portions of the display side of the chart body's rear wall. For example, one embodiment may feature a single door extending fully across the chart body from one side of the rear wall to the other in its closed position. In another single door embodiment, the slider track may be situated nearer one side of the chart body rather than at a widthwise center thereof, with one of the rails thus being defined by a respective side wall of the chart body, and the door being hinged at the other side wall to selectively close over the rear wall to the nearest rail.

FIGS. 7 and 8 show a further embodiment in which the growth chart device 10' features transparent doors 28' and a set of picture supports 50 that have been attached to the chart body 12 at the front side 14a of the rear wall thereof 14 to support a plurality of photographs 50. The doors 28' are of the same general structure of the first illustrated embodiment, only differing in that they don't have any any picture holders thereon, are made of transparent plastic, each incorporate integral hinge knuckle elements 54 at spaced positions along the lengthwise outer edge of the door 28' and each feature at least one magnetic door catch element 56 at a respective position along the lengthwise inner edge of the door 28'. The doors operate in the same manner as the first embodiment, being openable and closeable to selectively cover the front side 14a of the chart body rear wall 14 and any printed material, pictures, photographs or other information displayed thereon, but being transparent, does not conceal this such materials and information. The doors thus protect the contents of the chart, for example preventing dust buildup and fingerprint smudging on photographs mounted on the chart body, while still allowing viewing thereof.

The door-supported section(s) 54 of the knuckle of each hinge are formed as an integral part of the respective door, with the respective side wall of the chart body integrally defining the other chart-supported sections of the hinge knuckle. Adjacent knuckle sections on one piece are sufficiently spaced apart to accommodate each knuckle section on the opposing piece between them. Bores in the knuckle sections are provided to align with one another when the doors are installed on the chart in order to accommodate the pivot pin of the hinge in the necessary operable position for use of the resulting hinge.

The magnetic door catches keep each door secured in the closed position once initially closed. Each door catch features a magnetic piece on the respective rail 20 of the chart body and a corresponding piece of magnetically attractable material on the door 28', or vise versa. As such door catches are well known, they are not illustrated or described herein in any further detail. Other known door catch types may alternatively be employed in place of the magnetic device. A through hole 58 is provided in each door 28' at a position that proximate its movable inner edge so as to lie between the respective side wall and rail of the chart body when the door is closed, thereby forming a finger grip or handle that a user can manipulate to pull open the door. A handle or knob projecting outwardly from the door may alternatively be used in place of such a hole.

A plurality of picture support devices 60 accompany the growth chart device and are each individually fastenable to the front side 14a of the chart body's rear wall 14 on the side of the rails 20 opposite the measuring scale 26. Each picture support 60 is an elongated piece extending along a linear axis and having a T-shaped cross-section in planes normal to this lengthwise axis, as shown by the cross-sectional view of FIG. 8. The stem of the T-shape is equipped with a double sided adhesive at an end opposite the crossing portion of the T-shape, this adhesive preferably being in the form of a strip extending at least a substantial portion of the picture support's length. Initially, each picture support is provided with a peelable cover situated directly over the adhesive, so that the picture support is of a "peel and stick" configuration. To install the picture support on the chart body, a user peel's off the cover from over the adhesive strip and then presses this adhesive-carrying end of the support's T-shaped cross section flat against the flat front surface of the chart body's rear wall, which adhesively secures the picture support thereon.

As shown in FIGS. 7 and 8, a first picture support is secured on the chart body in a position extending horizontally along the chart's rear wall 14 at a height therealong where a user wishes to seat a first picture or photograph. The stem of the picture support's T-shaped cross section projects perpendicularly from the front surface of the chart's rear wall, and the crossing portion of T-shaped cross section extending perpendicularly across the end of the stem opposite the chart's rear wall extends vertically upward and downward from the projecting stem portion along a plane parallel to the flat rear wall of the chart. The upward projecting leg or half 60a of the crossing portion of the support's T-shape presents a picture retaining wall or lip so that when the bottom edge of a picture of photograph is seated on the ledge or shelf presented by the projecting stem portion 60b of T-shaped support, this bottom edge of the picture or photograph is blocked from sliding off the end of this ledge projecting from the rear wall.

With the photograph now seated on the first picture support with the back of the photograph, at least at the top edge thereof, resting against the front surface 14a of the chart's rear wall 14, the user then attaches a second picture support device to the chart's rear wall just above the top edge of the same photograph to lie parallel to the first support device at a distance upward therefrom. Like that of the first bottom support, the stem of the second support's cross-section projects outward from the chart's rear wall past the photograph when adhered to the wall. The downward depending leg or half 60*c* of the crossing portion of the second support's T-shape forms another retaining wall or lip that keeps the top edge of the photograph in place adjacent the front face of the chart's rear wall, much like the upward projecting portion of the first bottom support does for the photograph's bottom edge. The stem and the upward projecting leg or half of the crossing portion of the second support's T-shape respectively define the ledge or shelf and lower retaining element for another photograph to be secured on the chart body above the first photograph disposed between the first and lowermost two supports.

It will be appreciated that photograph or picture supports may be selectively fastenable to the chart body at any of a variety of possible heights therealong by way of attachment methods other than peel and stick adhesive. For example, picture supports sold with the growth chart device may feature hook or loop elements of a hook and loop fastener arrangement, with the front surface of the chart wall accordingly being provided with strips or pieces of the other element at heights along the area where photographs are to be supported. Having one or more continuous lengths of the fastener element fixed to this area of the chart body to extend vertically therealong allows fastening of a picture support at any selected height along the chart area intended for photographs or pictures, much like the use of adhesive-equipped supports attachable anywhere along a flat chart body surface. Despite the advantage of such arrangements giving the user free reign over where the picture supports are positioned, the chart may alternatively use other fastening arrangements in which fastening sites are defined only at predetermined intervals along the chart body from which the user can select in order to achieve a suitable photograph support site along the chart's height. It will also be appreciated that the shape of the supports may be altered, for example to have an L-shaped cross section in which the retaining portion projects only to one side of the projecting portion secured to the chart body. To secure both the top and bottom edges of each photograph with such supports would require two dedicated supports per photograph, whereas the T-shaped supports of the illustrated embodiment can reduce the number of supports needed, since the top support for one photograph can define the bottom support for another paragraph added just above the first.

As described herein above for the first embodiment, an owner or user of the chart may wish to position photographs of a child at vertical positions along the chart substantially aligned with positions along the scale where the child's height is or has been marked at the ages or time periods shown in the photographs. However, as a child will not necessarily grow in height enough within the time period between two photographs to accommodate the two photographs at heights aligned with the respective markers on the growth scale, a system of stickers or labels can be used to associate a particular photograph mounted on the chart to a particular height marker along the scale.

Such an arrangement is shown in FIG. 8, where a photograph label 62 having a particular number printed thereon is adhered to one of the photographs and a corresponding chart label 64 having the same number printed thereon is adhered to the marking area of the chart body adjacent a marking 66 having been made thereon to mark the child's height at the age or time period when that photograph was taken. Preprinted labels provided in pairs may be used, where the two labels of each pair have matching indicia printed thereon, for example two of the same letter, same number or same shape. Colour matching of labels in pairs may similarly be used, for example using labels with printed material thereon of matching colour, or using labels in which the display surface of the labels themselves in each pair match one another. Alternatively, blank labels may be used and labeled as desired in matching pairs by the owner/user. Numbered labels may be used in sequential order to mark the age or school grade of the child being measured.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A growth chart device comprising:
 a chart body presenting a wall side intended to face a wall or other vertical structure to which the growth chart is to be mounted and a chart side opposite said wall side;
 a measuring scale defined on the chart side of the chart body to extend along a lengthwise dimension of the chart body to be vertically oriented when mounted to the wall or other vertical structure;
 a marking area defined on the chart side of the chart body proximate the measuring scale to receive markings at different positions along the measuring scale at different times to track a height of an individual; and
 at least one door pivotally mounted on the chart body and movable between open and closed positions in which at least a portion of the chart side of the chart body is respectively uncovered and covered to give selective control over access to said portion.

2. The growth chart according to claim 1 wherein said portion of the chart side of the chart body selectively enclosable by the at least one door includes at least part of the measuring scale.

3. The growth chart according to claim 1 comprising a sliding indicator slidably mounted to the chart body for movement along the lengthwise dimension thereof to a position indicating the height of the individual along the measuring scale.

4. The growth chart according to claim 3 wherein the at least one door comprises a pair of doors mounted on the chart body to close over respective portions of the chart side of the chart body on opposite sides of the sliding indicator.

5. The growth chart according to claim 3 comprising a rail structure along which the sliding indicator is slidable and which projects from the chart side of the chart body past the sliding indicator to form a stop against which each door abuts in the closed position.

6. The growth chart according to claim 5 wherein the rail structure comprises a pair of opposing rails each having a track formed therein into which features of the sliding indicator project from between the opposing rails.

7. The growth chart according to claim 6 wherein at least one of the tracks comprises a through-slot in a respective one rail of the opposing rails.

8. The growth chart according to claim 3 wherein a projecting portion of the sliding indicator projects along the chart side of the chart body toward the measuring scale.

9. The growth chart according to claim 3 wherein a measuring arm of the sliding indicator is pivotable between storage and measuring positions extending along and projecting away from the chart side of the chart body respectively.

10. The growth chart according to claim 3 wherein the measuring scale and the marking area are defined on a same side of the sliding indicator.

11. The growth chart according to claim 3 wherein the sliding indicator is centrally located along a widthwise dimension of the chart body.

12. The growth chart device according to claim 1 comprising a display area defined on the chart side of the chart body on a side of a central lengthwise axis thereof opposite the marking area, wherein the at least one door comprise a pair of doors each arranged to selectively close over at least part of a respective one of the display and marking areas.

13. The growth chart according to claim 1 wherein each door is pivotable about an axis parallel to the lengthwise dimension of the chart body.

14. The growth chart according to claim 1 wherein each door is hinged to the chart body along a lengthwise edge of the chart body.

15. The growth chart according to claim 1 wherein the chart body has fastener holes passing therein for passage of fasteners therethrough from the chart side of the chart body to secure the device to the wall or other vertical structure.

16. The growth chart device of claim 1 in combination with a plurality of picture supports selectively attachable to the chart body on the chart side thereof at different positions along the lengthwise dimension of the chart body to support pictures thereon.

17. The growth chart device of claim 16 wherein each picture support has a cross-section presenting a projecting portion arranged to project outward from the chart side of the chart body when attached thereto and at least one retaining portion projecting to a respective side of the projecting portion to extend upward or downward along the chart side of the chart body when attached thereto.

18. The growth chart device of claim 17 wherein each photograph support comprises two retaining portions projecting to opposing sides of the projecting portion to extend upward and downward along the chart side of the chart body when attached thereto.

19. The growth chart device of claim 1 in combination with multiple pairs of labels, each pair comprising two labels having matching indicia for application of one of the two labels to a picture and the other of the two labels to a marked position along the measuring scale corresponding to a height of a person shown in the picture at a period of time when the picture was taken.

20. The growth chart device of claim 19 wherein the matching indicia of at least some of the pairs of labels comprises matching numbers.

* * * * *